(12) United States Patent
Roselli et al.

(10) Patent No.: US 11,076,945 B2
(45) Date of Patent: Aug. 3, 2021

(54) ENDOVASCULAR GRAFTS AND METHODS FOR EXTENDED AORTIC REPAIR

(71) Applicant: THE CLEVELAND CLINIC FOUNDATION, Cleveland, OH (US)

(72) Inventors: Eric E. Roselli, Rocky River, OH (US); Kelly B. Emerton, Bay Village, OH (US); Justin Metcalf, Cleveland, OH (US); Brandon Gulker, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 25 days.

(21) Appl. No.: 16/155,176

(22) Filed: Oct. 9, 2018

(65) Prior Publication Data
US 2019/0105149 A1   Apr. 11, 2019

Related U.S. Application Data

(60) Provisional application No. 62/683,334, filed on Jun. 11, 2018, provisional application No. 62/569,511, filed on Oct. 7, 2017.

(51) Int. Cl.
*A61F 2/07* (2013.01)
*A61F 2/92* (2013.01)
(Continued)

(52) U.S. Cl.
CPC .................. *A61F 2/07* (2013.01); *A61F 2/92* (2013.01); *A61F 2/89* (2013.01); *A61F 2/95* (2013.01);
(Continued)

(58) Field of Classification Search
CPC ...................................... A61F 2/07; A61F 2/92
See application file for complete search history.

(56) References Cited

U.S. PATENT DOCUMENTS 6,835,203 B1   12/2004   Vardi et al.
8,123,795 B1   2/2012   Knodel et al.
(Continued)

FOREIGN PATENT DOCUMENTS

EP   1208816 A2   5/2002
EP   1913897 A1   4/2008
(Continued)

OTHER PUBLICATIONS

Akasaka, Junetsu, et al. "Stent grafting technique using Matsui-Kitamura (MK) stent for patients with aortic arch aneurysm." European journal of cardio-thoracic surgery 27.4 (2005): 649-653.
(Continued)

*Primary Examiner* — Matthew W Schall
(74) *Attorney, Agent, or Firm* — Tarolli, Sundheim, Covell & Tummino LLP

(57) ABSTRACT

An endovascular graft including a stent graft and a surgical graft is provided. The stent graft can include an elongated body having a collapsed and expanded configuration and include a frame structure covered by a compression sleeve that retains the elongated body in the collapsed configuration until deployment of the stent graft. The endovascular graft can include a first cuff member sized and dimensioned to extend into a lumen of an aortic arch branch vessel when the endovascular graft is implanted in a subject. The frame structure can include a backstop sized and dimensioned to extend into the first cuff member when the endovascular graft is implanted in the subject. The surgical graft can be partially attached to the stent graft at a proximal end portion thereof.

8 Claims, 14 Drawing Sheets

(51) Int. Cl.

| | |
|---|---|
| A61F 2/966 | (2013.01) |
| A61F 2/97 | (2013.01) |
| A61F 2/95 | (2013.01) |
| A61F 2/89 | (2013.01) |
| A61F 2/82 | (2013.01) |
| A61F 2/06 | (2013.01) |

(52) U.S. Cl.
CPC ........... *A61F 2/97* (2013.01); *A61F 2002/061* (2013.01); *A61F 2002/828* (2013.01); *A61F 2002/9511* (2013.01); *A61F 2002/9665* (2013.01); *A61F 2220/0008* (2013.01); *A61F 2220/0075* (2013.01); *A61F 2250/0048* (2013.01)

(56) References Cited

U.S. PATENT DOCUMENTS

| | | | |
|---|---|---|---|
| 8,298,278 | B2 | 10/2012 | Gregorich et al. |
| 8,298,280 | B2 | 10/2012 | Yadin et al. |
| 8,932,340 | B2 | 1/2015 | Meyer et al. |
| 9,114,033 | B2 | 8/2015 | Feld et al. |
| 9,211,183 | B2 | 12/2015 | Ivancev et al. |
| 9,427,340 | B2 | 8/2016 | Yadin |
| 2003/0088305 | A1 | 5/2003 | Van Schie et al. |
| 2006/0173528 | A1 | 8/2006 | Feld et al. |
| 2007/0260304 | A1 | 11/2007 | Gregorich et al. |
| 2008/0177377 | A1 | 7/2008 | Meyer et al. |
| 2009/0030502 | A1 | 1/2009 | Sun et al. |
| 2009/0163994 | A1 | 6/2009 | Quigley et al. |
| 2009/0240318 | A1 | 9/2009 | Chalekian et al. |
| 2009/0287145 | A1 | 11/2009 | Cragg et al. |
| 2010/0131041 | A1 | 5/2010 | Lewis et al. |
| 2011/0153002 | A1 | 6/2011 | Davidson et al. |
| 2012/0221090 | A1 | 8/2012 | Wolf |
| 2013/0079870 | A1 | 3/2013 | Roeder et al. |
| 2013/0138203 | A1 | 5/2013 | Quadri |
| 2013/0158648 | A1 | 6/2013 | Hartley et al. |
| 2013/0345785 | A1 | 12/2013 | Hartley et al. |
| 2014/0180393 | A1 | 6/2014 | Roeder |
| 2014/0243952 | A1 | 8/2014 | Parodi |
| 2015/0164642 | A1 | 6/2015 | Khosravi et al. |
| 2015/0173920 | A1 | 6/2015 | Bruszewski et al. |
| 2016/0030209 | A1 | 2/2016 | Shalev et al. |
| 2016/0184115 | A1 | 6/2016 | Ondersma et al. |
| 2016/0310258 | A1* | 10/2016 | Wang ..................... A61F 2/844 |
| 2016/0346042 | A1 | 12/2016 | Nomiyama et al. |
| 2017/0007391 | A1 | 1/2017 | Inoue |
| 2017/0056152 | A1 | 3/2017 | Kelly |

FOREIGN PATENT DOCUMENTS

| | | |
|---|---|---|
| EP | 1946725 A1 | 7/2008 |
| EP | 2066269 A2 | 6/2009 |
| EP | 3090707 A1 | 11/2016 |

OTHER PUBLICATIONS

Criado, Frank J., et al. "Early Experience with the Talent™ Stent-Graft System for Endoluminal Repair of Abdominal Aortic Aneurysms." Texas Heart Institute Journal 27.2 (2000): 128.

Czerny, Martin, et al. "Initial results after combined repair of aortic arch aneurysms by sequential transposition of the supra-aortic branches and consecutive endovascular stent-graft placement." The Annals of thoracic surgery 78.4 (2004): 1256-1260.

Inglese, Luigi, et al. "Endovascular repair of thoracic aortic disease with the EndoFit stent-graft: short and midterm results from a single center." Journal of Endovascular Therapy 15.1 (2008): 54-61.

Ishimaru, Shin. "Endografting of the aortic arch." Journal of endovascular therapy 11.6_suppl (2004): II-62.

Kutty, Shelby, et al. "Endovascular stent grafts for large thoracic aneurysms after coarctation repair." The Annals of thoracic surgery 85.4 (2008): 1332-1338.

Lima, Brian, et al. "Modified and "reverse" frozen elephant trunk repairs for extensive disease and complications after stent grafting." The Annals of thoracic surgery 93.1 (2012): 103-109.

Mertens, Renato, et al. "Ventana fenestrated stent-graft system for endovascular repair of juxtarenal aortic aneurysms." Journal of Endovascular Therapy 19.2 (2012): 173-178.

Roselli, Eric E., et al. "Antegrade delivery of stent grafts to treat complex thoracic aortic disease." The Annals of thoracic surgery 90.2 (2010): 539-546.

PCT Invitation to Pay Additional Fees for PCT/US2015/049301, dated Nov. 9, 2015, pp. 1-5.

PCT International Search Report and Written Opinion for corresponding PCT International Application Serial No. PCT/US201/054971, dated Feb. 28, 2019, pp. 1-17.

* cited by examiner

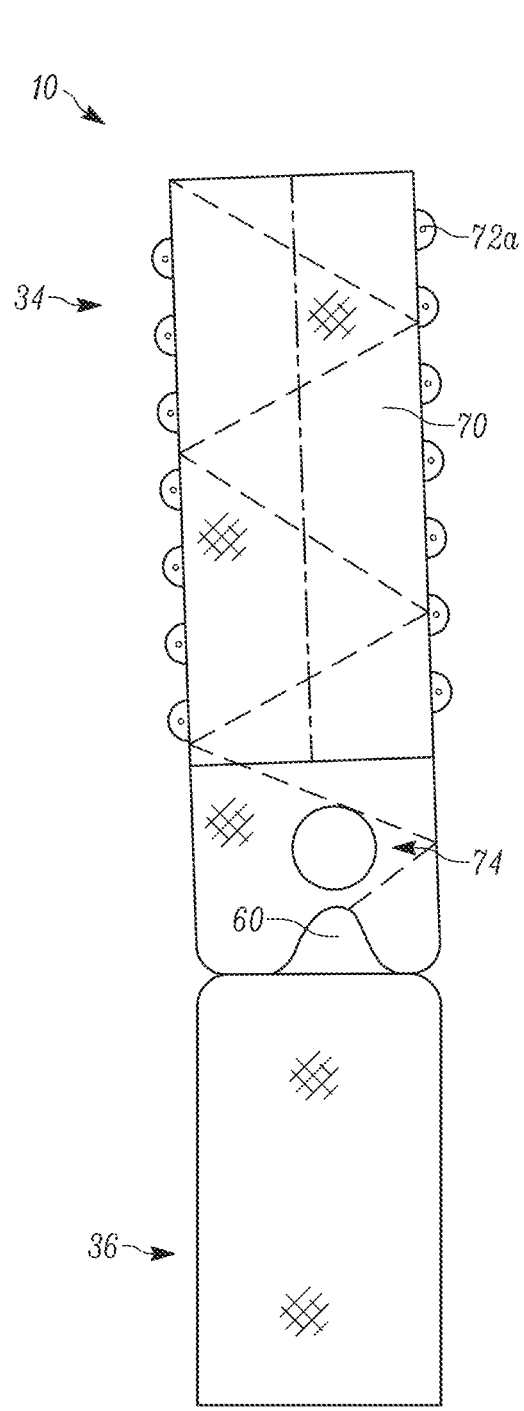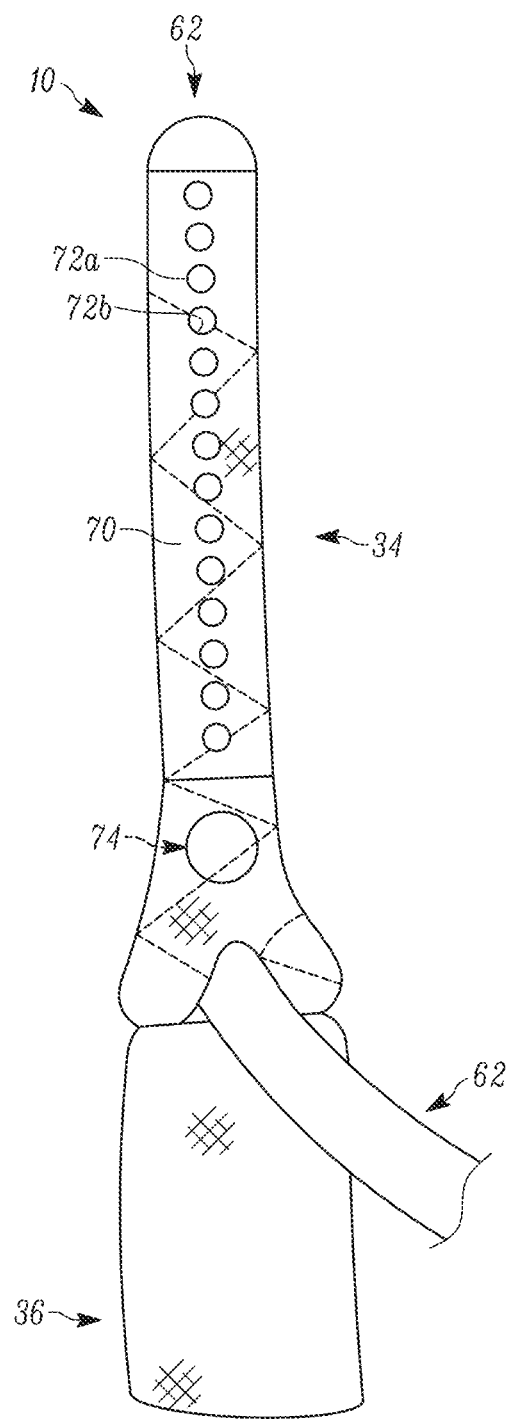
FIG. 6A
FIG. 6B

ENDOVASCULAR GRAFTS AND METHODS FOR EXTENDED AORTIC REPAIR

CROSS-REFERENCE TO RELATED APPLICATIONS

The present application claims priority to U.S. Provisional Application No. 62/683,334, filed on Jun. 11, 2018 and U.S. Provisional Application No. 62/569,511, filed on Oct. 7, 2017. The content of both applications are incorporated by reference in their entirety.

TECHNICAL FIELD

The present disclosure relates generally to vascular repair of bodily vessels, and more particularly to endovascular grafts and related methods for repairing aortic abnormalities.

BACKGROUND

A leading cause of disability and death in both the U.S. and abroad includes damage to a portion of the vascular system. This is a particular problem with regard to aortic aneurysms. Diseases of the aorta, for example, are becoming an increasing concern as a result of advancements in cardiac surgery and human longevity. Severe arterial sclerosis, severely calcified aorta, and other indications continue to necessitate complete or partial aortic replacement procedures.

Aneurysms are typically characterized by diseased or damaged blood vessels which lead to a weakening of the vessel wall. Weakening of the vessel wall can then lead to a blood-filled dilation of the vessel. Left untreated, aneurysms will eventually rupture and result in acute (and often fatal) hemorrhaging in a very short period of time.

The aorta has numerous arterial branches. The arch of the thoracic aorta, for example, has three major branches arising from the convex upper surface of the arch and ascending through the superior thoracic aperture to the root of the neck. The proximity of an aneurysm to a branch artery may limit the use of an excluding device, such as a tubular stent graft. For example, the main body or ends of a tubular stent graft may occlude or block the branch arteries as a result of positioning the stent graft against a healthy, i.e., non-diseased or dilated portion of the artery wall. Additionally, there may be an inadequate length of healthy tissue for the stent graft to seal against in the area between the aneurysm and the location of the branch arteries. Even if the stent graft is initially located without blocking a branch artery, there still is a risk that the devices will migrate to a position where it may partially or fully block a branch artery.

SUMMARY

One aspect of the present disclosure can include an endovascular graft. The endovascular graft can include a stent graft that is attached to a surgical graft. The stent graft can include an elongated body movable between collapsed and expanded configurations. The body can have proximal and distal end portions an intermediate portion extending between the proximal and distal end portions, and a lumen extending between the proximal and distal end portions. The body can further include a frame structure having at least a portion thereof covered by a compression sleeve that retains the body in the collapsed configuration until deployment of the stent graft is needed. A first cuff member can be attached to the elongated body so that a lumen of the first cuff member is in fluid communication with the lumen of the elongated body. The first cuff member can be sized and dimensioned to extend into a lumen of an aortic arch branch vessel when the endovascular graft is implanted in a subject. The elongated body of the stent graft can include an aperture in fluid communication with the lumen of the elongated body and the lumen of the first cuff member. The aperture can be defined by a portion of the frame structure. The frame structure can include a backstop sized and dimensioned to extend into the lumen of the first cuff member when the endovascular graft is implanted in the subject. The surgical graft can be partially attached to the stent graft at the proximal end portion thereof. A proximal end of the surgical graft can include a sewing cuff attached thereto.

Another aspect of the present disclosure can include a method for repairing at least a portion of a diseased aortic arch in a subject. One step of the method can include providing an endovascular graft comprising a stent graft that is partially attached to a surgical graft. The stent graft can comprise an elongated body and a first cuff member. The stent graft can have a proximal end portion, a distal end portion, an intermediate portion extending between the proximal and distal end portions, and a lumen extending between the proximal and distal end portions. The elongated body can further include a frame structure having at least a portion thereof covered by a compression sleeve. The first cuff member can be attached to the elongated body so that a lumen of the first cuff member is in fluid communication with the lumen of the elongated body. The elongated body can include an aperture in fluid communication with the lumen of the elongated body and the lumen of the first cuff member. The aperture can be defined by a portion of the frame structure. The frame structure can include a backstop. The stent graft can be positioned, in a collapsed configuration, in the aortic arch of the subject. The first cuff member can be positioned in an aortic branch vessel, such as the left subclavian artery. The compression sleeve can be actuated so that the stent graft expands into the distal aortic arch and the first cuff member extends into the aortic arch branch vessel. For example, the compression sleeve about the first cuff member can be actuated first and then the compression sleeve of the stent graft can be actuated. The stent graft can be secured in the distal aortic arch. The surgical graft can be secured to a transected edge of the aorta.

Another aspect of the present disclosure can include a delivery system for delivering an endovascular graft. The delivery system can include a handle comprising an elongated body having a proximal portion and a distal portion with a distal end defining a distal aperture. A secondary support guide channel can extend longitudinally within the elongated body having one end in fluid communication with a secondary support guide aperture defined by the proximal portion of the elongated body and another end in fluid communication with the distal aperture. The handle can also include a first actuator channel having one end in fluid communication with a first actuator aperture defined by the elongated body and another end in fluid communication with a distal first actuator aperture defined by the distal end of the elongated body. The handle can also include a second actuator channel having one end in fluid communication with a second actuator aperture defined by the elongated body and another end in fluid communication with the distal aperture.

The delivery system can also include a first actuator comprising a knob and a wire extending from the knob. The wire can slidably extend through the first actuator aperture, the first actuator channel and the distal first actuator aperture. The delivery system can further include a second actuator that also comprises a knob and a wire extending from the knob. The wire can slidably extend through the second actuator aperture, the second actuator channel, and the distal aperture.

The delivery system can also include a primary flexible support guide directly or indirectly connected to the distal end of the handle and having a blunt atraumatic tip. In certain embodiments, a rigid support rod can be disposed between the primary flexible support guide and the handle. For example, one end of the rigid support rod can be connected to the distal end of the handle and another end can be connected to the proximal end of the primary flexible support guide. An elongate secondary support guide can slidably extend through the secondary support guide aperture, the secondary support guide channel and the distal aperture.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIGS. 6A and 6B are top views of the endovascular graft of FIGS. 2A and 2B respectively;

DETAILED DESCRIPTION

Definitions

Figure 1:
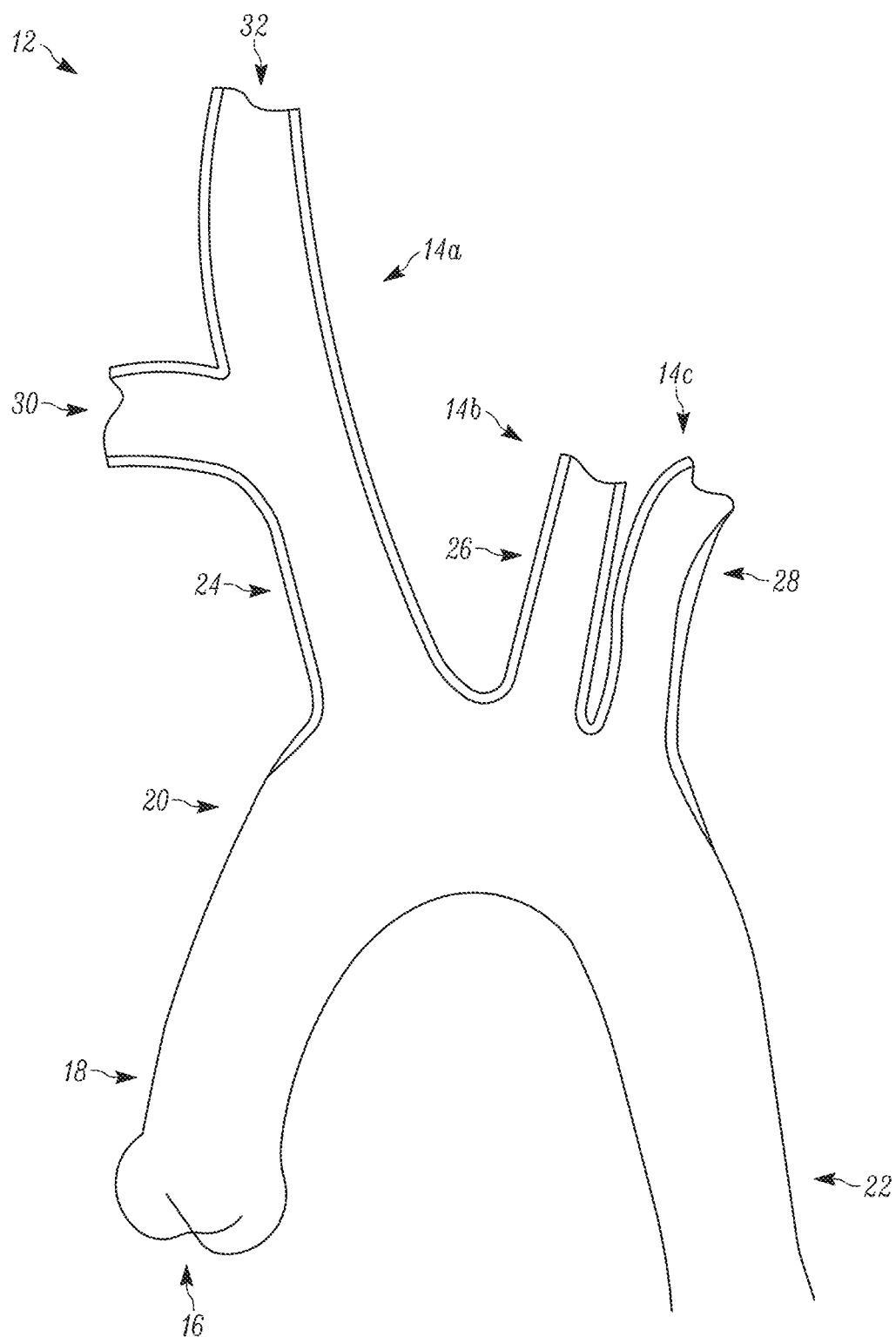
FIG. 1 is a cross-sectional view of an aortic arch and arch vessels.

Unless otherwise defined, all technical terms used herein have the same meaning as commonly understood by one of ordinary skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

By "integral," "integrated" or "unitary" is meant that the described components are fabricated as one piece during manufacturing or the described components are otherwise not separable using a normal amount of force without damaging the integrity (i.e. tearing) of either of the components. A normal amount of force is the amount of force a user would use to remove a component meant to be separated from another component without damaging either component.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, etc.

As used herein, the term "biocompatible" can refer to a material that is substantially non-toxic in the in vivo environment of its intended use, and that is not substantially rejected by a patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

As used herein, the term "endoleak" can refer to the presence of blood flow past the seal between the end of a stent graft and the vessel wall (Type I), and into the aneurysmal sac, when all such flow should be contained within the stent graft's lumen.

As used herein, the term "migration" can refer to displacement of a stent graft from its intended implantation site.

As used herein, the terms "placed stent graft" or "implanted stent graft" can refer to a surgically placed or implanted stent graft, either by invasive or non-invasive techniques.

Anatomy and Physiology

To assist the reader in understanding the relevant anatomy and physiology to which certain aspects of the present disclosure pertain, FIG. 1 illustrates a cross-sectional view of a human aorta 12 and accompanying arch vessels, including the aortic arch branch vessels 14. The aorta is the largest vessel in the body. It transports oxygenated blood from the left ventricle of the heart (not shown) to every organ. The aorta starts in the heart with the aortic valve 16, which is immediately adjacent the aortic root 18 and followed by the ascending aorta 20, the transverse aorta 12 or aortic arch, the descending aorta 22, and the thoracoabdominal aorta (not shown). The aorta ends in the abdomen after bifurcation of the abdominal aorta in the two common iliac arteries (not shown). The aortic arch 12 gives off the brachiocephalic trunk 24, the left common carotid artery 26, and the left subclavian artery 28. The brachiocephalic trunk 24 splits to form the right subclavian and the right common carotid arteries 30 and 32, which supply blood to the right arm and the right side of the neck and head. The left common carotid artery 26 and left subclavian artery 28 perform parallel functions on the left side.

Endovascular Grafts

One aspect of the present disclosure can include an endovascular graft 10 (FIGS. 2A-2B) for implantation in, and repair of, a diseased blood vessel, such as a diseased aortic arch. The endovascular graft 10 can comprise a stent graft 34 that is partially connected or attached to a surgical graft 36. By "partially connected", it is meant that the stent graft 34 is connected or attached to the surgical graft 36 at one or more points 38 (e.g., by a suture or sutures) such that a lumen 40 of the stent graft is not in fluid communication with a lumen 42 of the surgical graft when the endovascular graft 10 is not implanted in a subject. In other words, an edge 44 of the stent graft 34 is not entirely in contact with, flush with, or sealed against a corresponding leading edge 46 of the surgical graft 36.

Figure 2A:
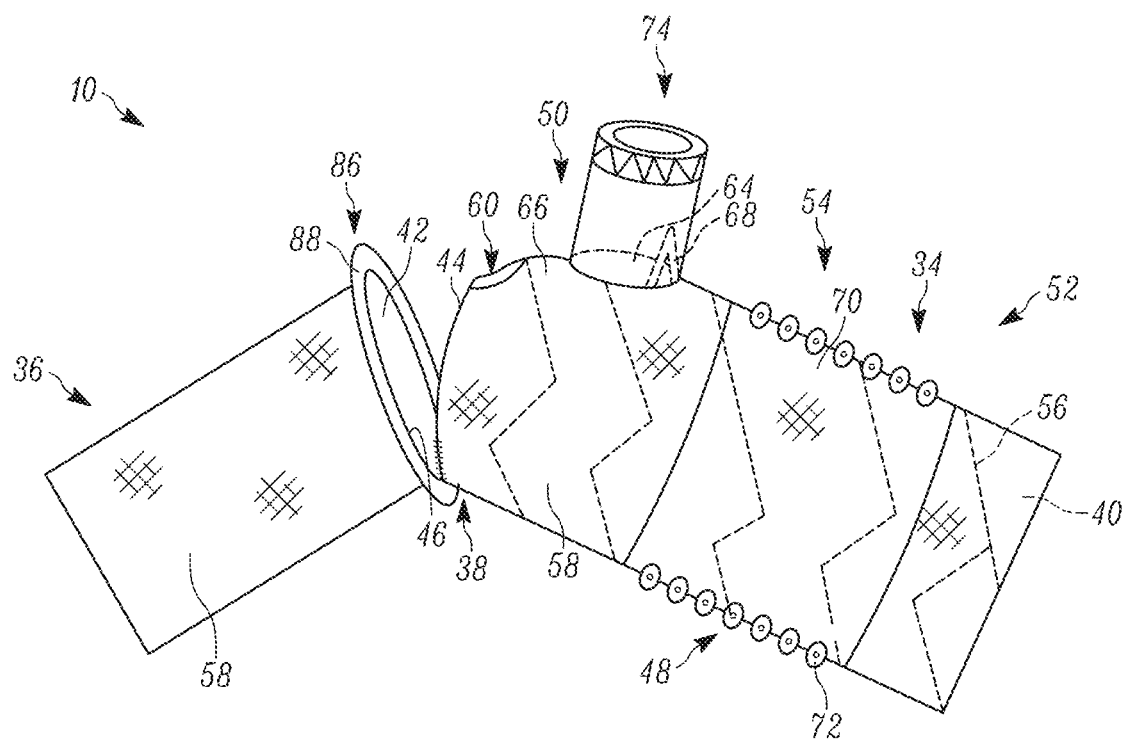
FIGS. 2A-B are side views of an endovascular graft according to an aspect of the present disclosure in an expanded configuration (FIG. 2A) and a collapsed configuration (FIG. 2B)
Figure 2B:
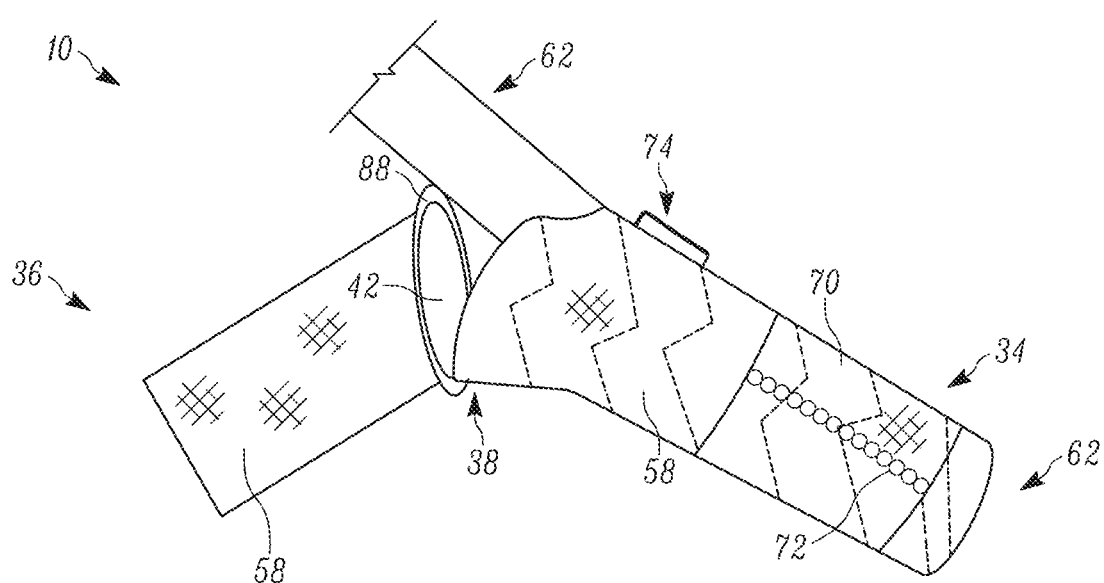

As shown in FIGS. 2A-2B, the stent graft 34 is movable between an expanded configuration (FIG. 2A) and a collapsed configuration (FIG. 2B). The stent graft 34 can comprise an elongated body 48 having a proximal end portion 50, a distal end portion 52, an intermediate portion 54 extending between the proximal and distal end portions, and a lumen 40 extending between the proximal and distal end portions. In some instances, the stent graft 34 can have a flexible, tube-like configuration and be adapted for placement in a bodily vessel, such as an aortic arch 12. The stent graft 34 can be configured to engage an inner surface of a bodily vessel so that the elongated body 48 thereof forms a complete or substantial seal with the inner surface of the bodily vessel.

In another aspect, the elongated body 48 can include or comprise a frame structure 56. In some instances, the frame structure 56 can extend along and define the entire length of the elongated body 48. The frame structure 56 can be constructed and dimensioned as disclosed in U.S. patent application Ser. No. 14/849,785, filed Sep. 10, 2015 (hereinafter, "the '785 application"), incorporated by reference in its entirety (including col. 5, line 35 to col. 9, line 22). In other instances, the frame structure 56 can extend along and define less than the entire length of the elongated body 48. For example, the proximal end portion 50 of the elongated body 48 can include a frame structure 56 while the intermediate portion 54 and/or distal end portion 52 of the body can include an expandable support member (not shown). Examples of expandable support members are described in the '785 application.

Figure 3:
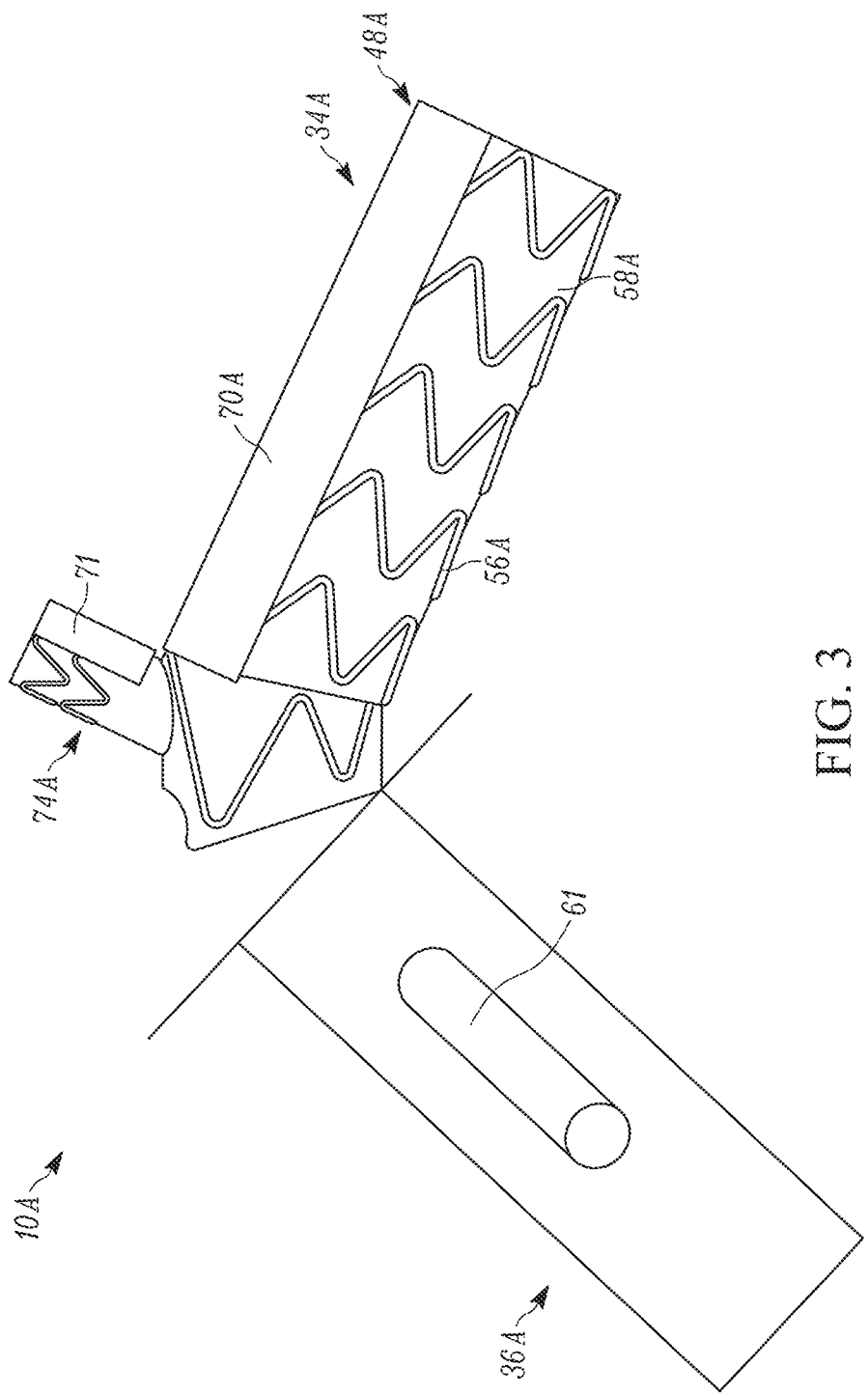
FIG. 3 is a side view of an endovascular graft according to an aspect of the present disclosure in an expanded configuration.

Each of the frame structure 56 and the expandable support member (if present) can be stitched into or otherwise attached to a biocompatible graft material 58 comprising all or only a portion the stent graft 34. Each of the frame member 56 and the expandable support member (if present) can have at least one surface thereof covered by the graft material 58. Referring to FIG. 3, in certain embodiments, a frame structure 56A is disposed on the outer surface of a biocompatible graft material 58A of the stent graft 34A of an endovascular graft 10A.

The graft material 58 can include any biocompatible material that is mechanically stable in vivo and is capable of preventing or substantially reducing the possibility of the passage or flow of blood or other body fluids through the stent graft 34. Examples of suitable materials for use in constructing the stent graft 34 can include biocompatible plastics, such as woven polyester, non-resorbable elastomers or polymers, such as silicone, SBR, EPDM, butyl, polyisoprene, Nitril, Neoprene, nylon alloys and blends, poly(ethylene-vinyl-acetate) (EVA) copolymers, silicone rubber, polyamides, polyurethane, poly(ester urethanes), poly(ether urethanes), poly(ester urea), polypropylene, polyethylene, polycarbonate, polytetrafluoroethylene (PTFE) (e.g., TEFLON), expanded PTFE (ePTFE), polyethylene terephthalate (e.g., DACRON), and polyethylene copolymers. It will be appreciated that the stent graft 34 can additionally or optionally include a layer of biological material (not shown), such as bovine or equine pericardium, peritoneal tissue, an allograft, a homograft, a patient graft, or a cell-seeded tissue. The layer can cover the entire stent graft 34 or only a portion thereof. One skilled in the art will appreciate that other materials suitable for vascular surgical applications may also be appropriate for the stent graft 34.

Figure 4:
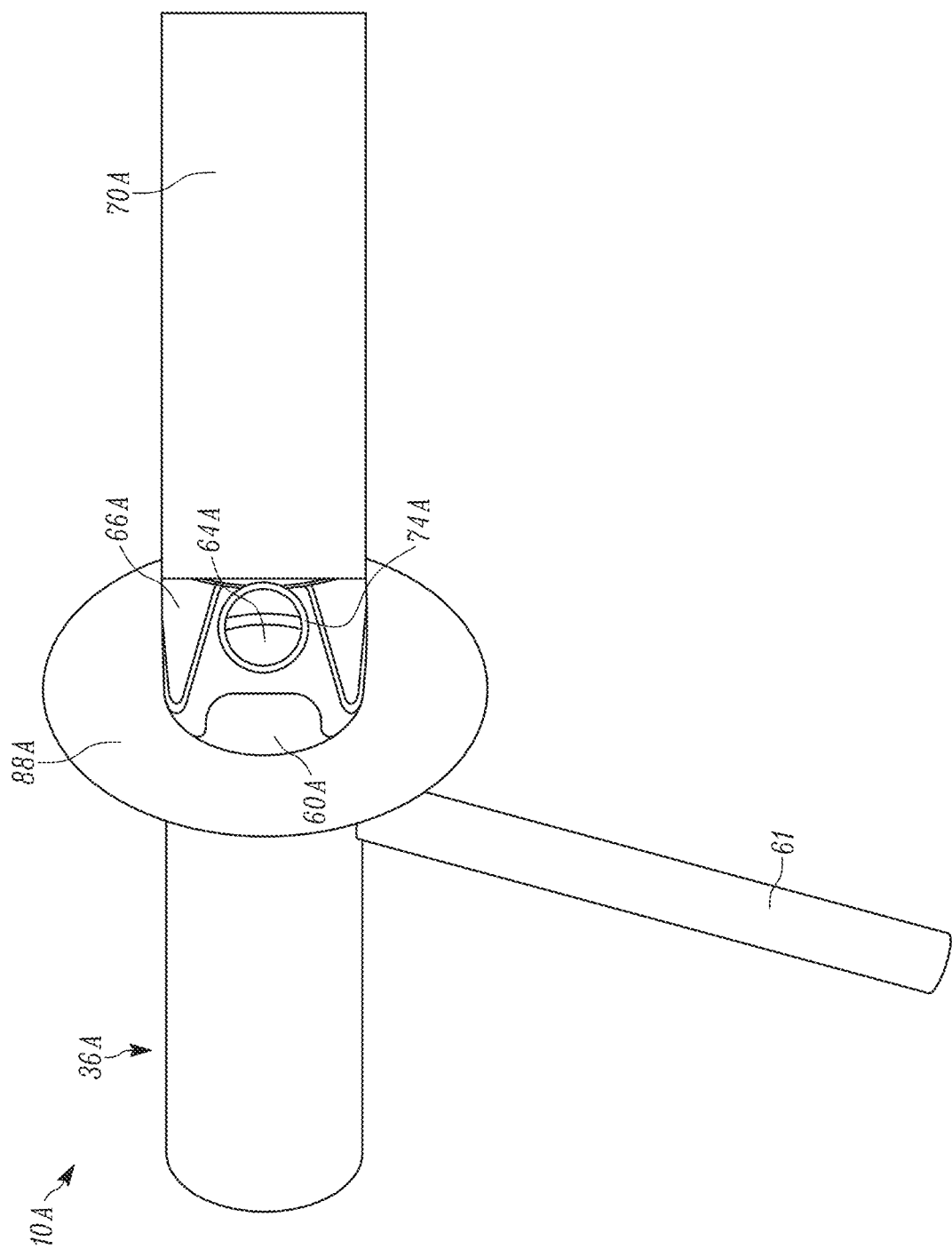
FIG. 4 is a top view of the endovascular graft of FIG. 3.

The proximal end portion 50 of the elongated body 48 can include a scallop opening 60 (FIGS. 6A-B and FIG. 4). The scallop opening 60 is defined by an arch-shaped opening that is sized and dimensioned to accommodate a delivery tool 62

(not shown in detail). Sewing cuff 88 (described in more detail below) can also include a scallop opening having an arch-shape that is sized and dimensioned to accommodate the delivery tool. In such instance, the scallop opening of the sewing cuff and the elongated body can oppose each other and collectively define an aperture to maintain blood flow to head vessels and the upper extremities of the subject. For example, advantageously, the scallop opening(s) gives the physician a greater amount of control in accommodating the innominate and carotid vessels (not shown).

In another aspect, the stent graft 34 can include an aperture 64 (FIG. 2A and FIG. 4). In one example, the aperture 64 can be located about an upper portion 66 of the proximal end portion 50. The aperture 64 can be sized and dimensioned so that the lumen 40 of the elongated body 48 is in fluid communication with the aperture 64. The aperture 64 can have any desired length, width and/or circumference. In some instances, the aperture 64 can have an elongated, oval-like shape; however, it will be appreciated that other shapes are possible.

Figure 5:
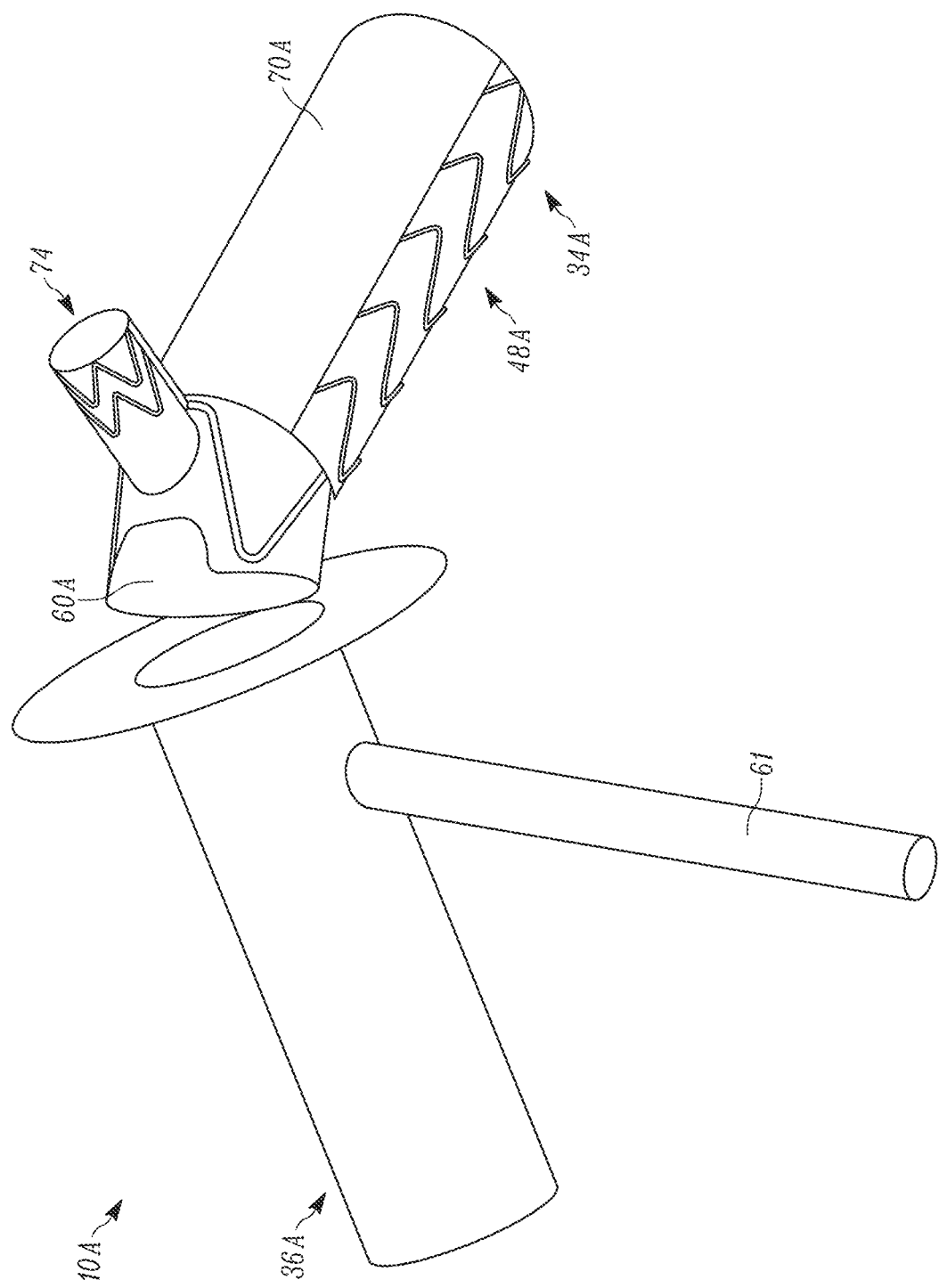
FIG. 5 is a perspective view of the endovascular graft of FIG. 3.
Figure 7:
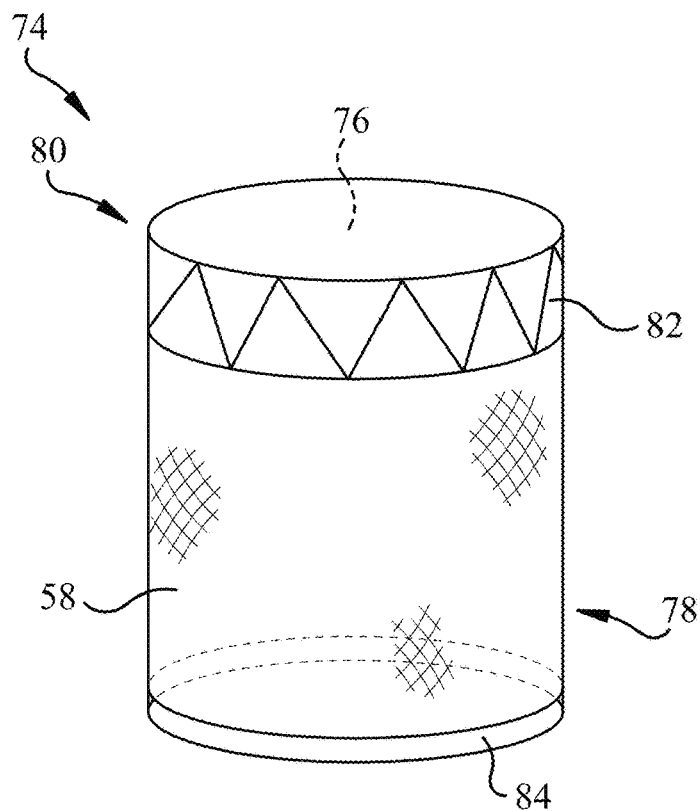
FIG. 7 is a perspective view of a first cuff member of an endovascular graft of FIGS. 2A-2B.

The stent graft 34 can include a first cuff member 74 attached to the elongated body 48 (e.g., at the proximal end portion 50 thereof) so that a lumen 76 of the first cuff member is in fluid communication with the lumen 40 of the elongated body 48 (e.g., via the aperture 64). The first cuff member 74 can be sized and dimensioned to extend into a lumen of an aortic arch branch vessel, such as the left subclavian artery 28 when the endovascular graft 10 is implanted in a subject. As shown in FIG. 7, the first cuff member 74 can have a tubular or cylindrical-shaped configuration and include a first end portion 78 and a second end portion 80. The lumen 76 can extend between the first and second end portions 78 and 80. The first cuff member 74 can be made of a biocompatible material 58 that covers one or more surfaces of an expandable support member 82 and a base ring 84. The expandable support member 82 and the base ring 84 can be located at the second and first end portions 80 and 78, respectively. The base ring 84 can encircle aperture 64 defined by the frame structure 56. The base ring 84 can assist in attaching the first cuff member 74 to the elongated body 48 (e.g., using sutures). The expandable support member can comprise a stent as illustrated in FIGS. 3-5.

The stent graft 34 can include a backstop 68 that is similar or identical to the backstop described in the '785 application, which is incorporated in reference herein (including col. 5, line 35 to col. 9, line 22). The backstop 68 can be adapted to extend into the lumen 76 of the first cuff member 74 when the endovascular graft 10 is implanted in a subject. In some instances, the backstop 68 can be heat-set in a raised position so that it is at a designated angle relative to the elongated body 48 of the stent graft 34, and is a portion of the frame structure 56. Advantageously, the backstop 68 can provide axial alignment of the endovascular graft 10 relative to the left subclavian artery 28 as well as rotational orientation for the endovascular graft to align with the branch vessels 14. Additionally, the backstop 68 can ensure lumen patency (of the first cuff member 74) following implantation of the endovascular graft 10 and can also reduce the risk of endoleaks.

Figure 8:
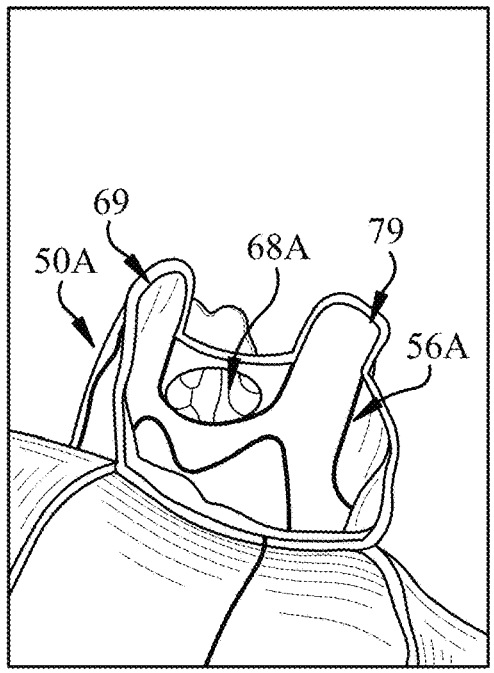
FIGS. 8 and 9 and are top views depicting an embodiment of a frame structure disposed within a portion of a stent graft of an endovascular graft according to an aspect of the present disclosure.
Figure 9:
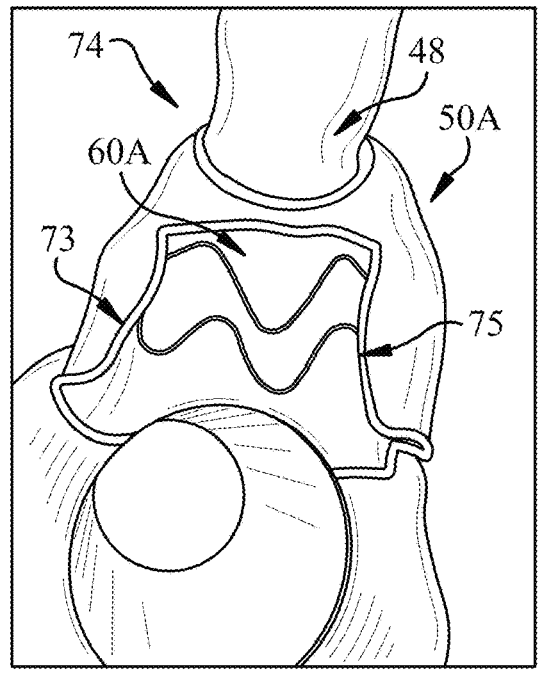

In another aspect, and with reference to FIGS. 8 and 9, frame structure 56A can comprise a continuous frame that includes backstop 68A located between arch-shaped frame segments 69 and 79. Arch-shaped frame segments 69 and 79 can be sutured or otherwise secured to the proximal edges 73 and 77 of proximal end portion 50A of the stent graft. Proximal edges 73 and 77 partially define opening 60A and can be in communication with the brachiocephalic artery and the left common carotid artery when the endovascular graft is implanted. Arch-shaped frame segments 69 and 79 of frame structure 56A can help maintain patency of the proximal end portion 50A of the stent graft when implanted in the aortic arch.

All or only a portion of the elongated body 48 of the stent graft 34 can include a compression sleeve 70 that covers the frame structure 56 and/or the expandable support member (if present). The compression sleeve 70 can comprise a biocompatible material 58, as discussed above. In some instances, the sleeve 70 can overlay the biocompatible material 70 that is already present about the frame structure 56 and/or expandable support member (if present). In other words, the sleeve 70 can comprise a separate piece of material 58 from the material covering the frame structure 56 and/or expandable support member. In other instances, the compression sleeve 70 can be in direct contact with the frame structure 56 and/or expandable support member (if present) as depicted in FIGS. 3-5. For example, the compression sleeve can be attached at either of its major edges to separate pieces of biocompatible material 58 already covering the remainder of the frame structure 56 and/or expandable support member.

The compression sleeve 70 can retain the elongated body 48 in the collapsed configuration until deployment of the stent graft 34 is needed (e.g., after implantation of the endovascular graft 10). As shown in FIGS. 6A-B, the compression sleeve 70 can include a plurality of eyelets 72 or fastening mechanisms attached thereto. To place the stent graft 34 in the collapsed configuration, the eyelets 72 can be aligned with another (FIG. 6B), which causes the sleeve 70 to compress and decrease the diameter of the elongated body 48. When the eyelets 72 are aligned, a suture, wire, or other similar mechanism (not shown) can be threaded through each of the eyelets to maintain the stent graft 34 in the collapsed configuration. When expansion of the stent graft 34 is desired, the suture or wire can be withdrawn through the eyelets 72, thereby allowing the frame structure 56 and/or expandable support member (and thus the elongated body 48) to transition into the expanded configuration as depicted in FIG. 6A.

Further, referring to FIG. 3, which depicts an embodiment of an endovascular graft 10A in an expanded configuration, elongated body of 48A of stent graft 34A can have a separate compression sleeve than first cuff member 74A. For example, elongated body 48A can have a compression sleeve 70A wrapped around or otherwise disposed thereabout elongated body 48A and first cuff member 74A can have a separate compression sleeve 71 wrapped around or otherwise disposed thereabout first cuff member 74A. During deployment of endovascular graft 10A, compression sleeve 71 can be retracted or "unlaced" such that compression sleeve 71 lays flat against a side of first cuff member 74A and compression sleeve 70A can be retracted or "unlaced" such that compression sleeve 70A lays flat against a side of elongated body 48A as illustrated in FIG. 3. As described in more detail, an actuator wire can be connected to the distal end (such as the distal most end) of compression sleeves 70A and 71 to deploy elongated body 48A and first cuff member 74A by effectively unlacing sleeves 70A and 71 thereby allowing elongated body 48 and first cuff member 74A to assume an expanded configuration.

In some instances, similar to the compression sleeve of the elongated body, the compression sleeve disposed about the first cuff member can include one or more interlocking members (not shown) that constrain the diameter of the first cuff member when locked together using a constraint wire, as described in more detail below. The constraint wire can be removed during the deployment procedure at which point the diameter of the first cuff member expands. Advantageously, the compression sleeve provides an improved deployment sequence that provides sufficient diameter constraint while minimizing the number of components that need to be retracted from the endovascular graft following implantation. This minimizes the risk of components migrating or becoming dislodged during retraction.

Figure 11:
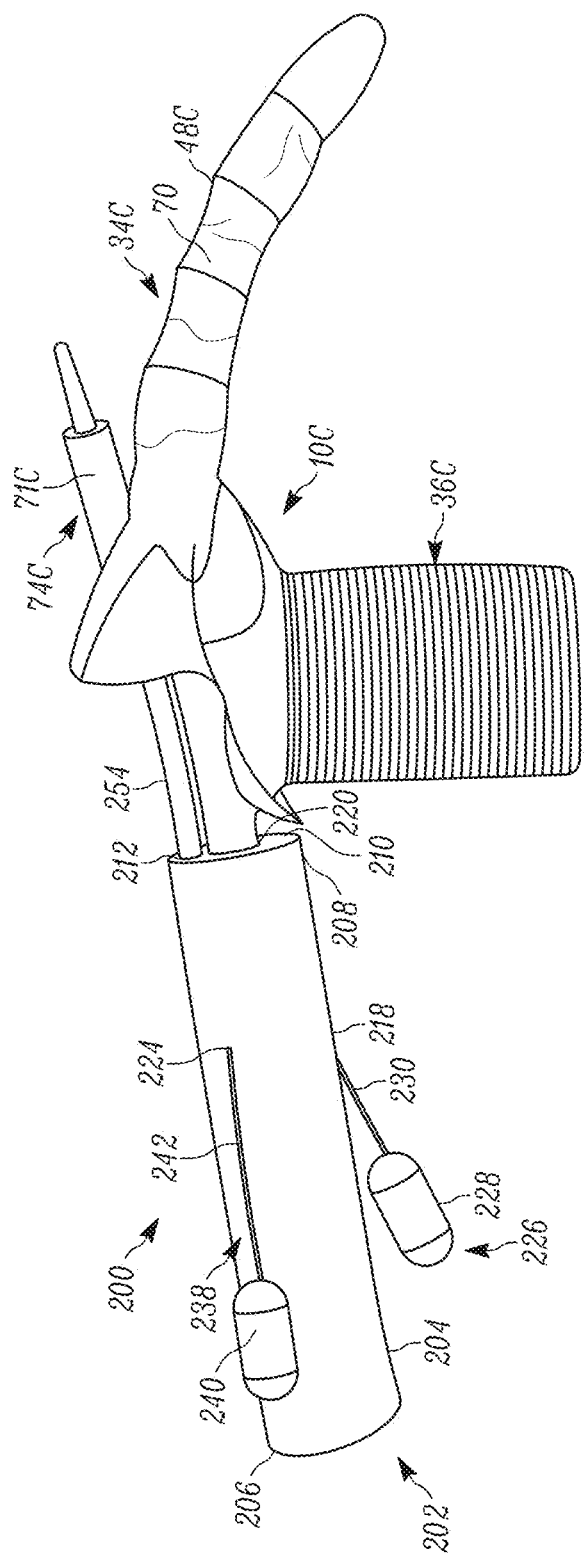
FIG. 11 is a side view of an endovascular graft with a stent graft and a first cuff member loaded on a delivery system according to an aspect of the present disclosure.

FIG. 11 illustrates a compression sleeve 71C covering first cuff member 74C. As described in more detail, an actuator wire can be connected to the distal end (such as the distal most end) of compression sleeve 75 to deploy first cuff member 74C by effectively unlacing sleeve 75 thereby allowing first cuff member 74C to assume an expanded configuration.

The compression sleeve can have a variety of shapes and dimensions, and is not necessarily limited to a rectangular configuration as shown in the Figures. Additionally, more than one sleeve can be used to form the stent graft.

Advantageously, the compression sleeve(s) provides an improved deployment sequence that provides sufficient diameter constraint while minimizing the number of components that need to be retracted from the endovascular graft following implantation. This minimizes the risk of components migrating or becoming dislodged during retraction. Further, compression sleeve(s) can provide the added benefit of improved seal of proximal descending entry or reentry tears, which most commonly occur along the greater curve of the descending portion of the aorta.

The endovascular graft 10 can include a surgical graft 36 partially attached to the stent graft 34 at a proximal end portion 86 thereof. The surgical graft 36 can be made of a biocompatible material 58 and have a generally tubular or cylindrical shape. The surgical graft 36 can include a leading edge 46, at least a portion of which is adapted for attachment to a transected edge of an aorta (e.g., an ascending aorta 20) or an aortic arch 12. The surgical graft 36 can include a sewing cuff 88 attached to the proximal end portion 86. The sewing cuff 88 can have a circular or oval-like shape and be adapted for suturing to a portion of a bodily vessel, such as a transected edge of an aorta (e.g., an ascending aorta 20) or an aortic arch 12. The sewing cuff 88 can be securely attached to the surgical graft 36 using any one or combination of known attachment means (e.g., staples, clips, sutures, adhesives, etc.). The sewing cuff 88 can be comprised of any suitable biocompatible material including, for example, woven polyester, DACRON, TEFLON, PTFE and/or any one or combination of the biocompatible materials 58 disclosed above. Advantageously, the sewing cuff 88 can aide in sewing to native tissue and reduces the amount of suturing required during surgical implantation of the endovascular graft 10 while still allowing the physician to control the precise location on the native tissue to suture the endovascular graft. As shown in FIGS. 3-5, a surgical graft 36A of an endovascular graft 10A can include conduit 61 sized and dimensioned to be attached to a cardiopulmonary bypass machine.

Figure 10:
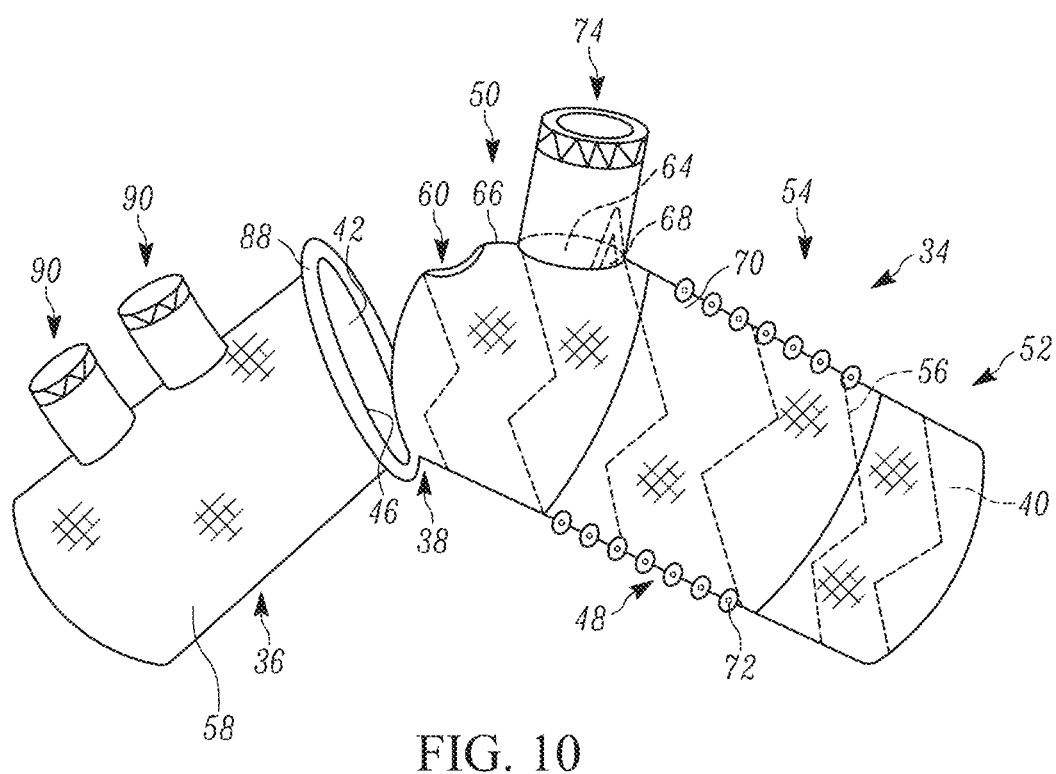
FIG. 10 is a side view of an alternative configuration of the endovascular graft of FIGS. 2A-2B.

In another aspect, an endovascular graft 11 can be constructed as shown in FIG. 10. The endovascular graft 11 can be identically constructed as the endovascular graft 10 in FIGS. 2A-2B, except where described below. For example, the surgical graft 36 can include second and third cuff members 90 and 92. The second and third cuff members 90 and 92 can be identically or similarly constructed as the first cuff member 74. The second and third cuff members 90 and 92 can be spaced apart from one another and sized and dimensioned for insertion into the left common carotid artery 26 and the brachiocephalic trunk 24, respectively. It will be appreciated that the surgical graft 36 can be alternatively constructed to include only the second cuff member 90 or only the third cuff member 92.

Delivery Systems

Figure 12:
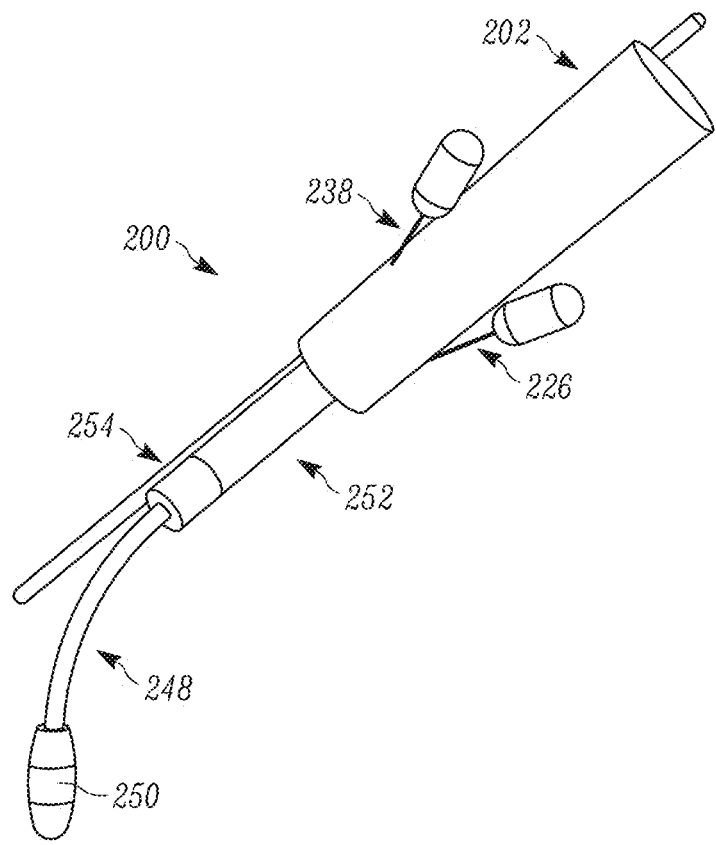
FIG. 12 is a top view of a delivery system according to an aspect of the present disclosure.
Figure 13:
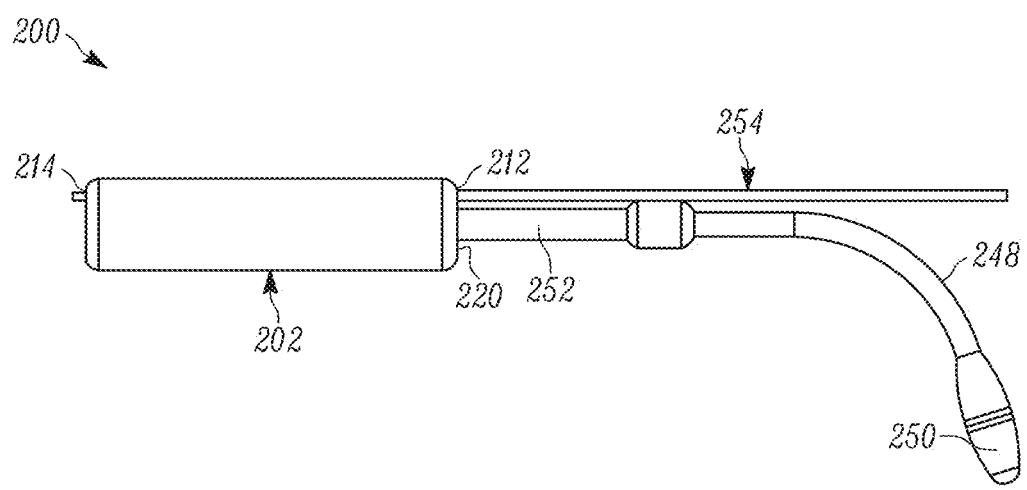
FIG. 13 is a side view of components of a delivery system according to an aspect of the present disclosure.

Referring to FIGS. 11-13, certain aspects of the present disclosure can include a delivery system to deliver an endovascular graft. A delivery system 200 can include a handle 202 comprising an elongated body 204 having a proximal portion 206 and a distal portion 208 with a distal end 210 defining a distal aperture 212. A secondary support guide channel (not shown) can extend longitudinally within elongated body 204 having one end in fluid communication with a secondary support guide aperture 214 (shown in FIG. 13) defined by proximal portion 206 of elongated body 204 and another end in fluid communication with distal aperture 212. Handle 202 can also include a first actuator channel (not shown) having one end in fluid communication with a first actuator aperture 218 defined by elongated body 204 and another end in fluid communication with a distal first actuator aperture 220 defined by distal end 210 of elongated body 204. Handle 202 can further include a second actuator channel (not shown) having one end in fluid communication with a second actuator aperture 224 defined by elongated body 204 and another end in fluid communication with distal aperture 212.

Delivery system 200 can also include a primary flexible support guide 248 directly or indirectly connected to distal end 210 of handle 202 and having a blunt atraumatic tip 250. In a loaded configuration, elongated body 48C of stent graft 34C is disposed about primary flexible support guide 248. Primary flexible support guide 248 can allow stent graft 34C to be manipulated within the aorta to allow accurate positioning of stent graft 34C. An elongate secondary support guide 254 can slidably extend through secondary support guide aperture 214, the secondary support guide channel and distal aperture 212. In a loaded configuration, first cuff member 74C is disposed about a distal portion of elongate secondary support guide 254. A guide wire can extend through a lumen of the elongate secondary support guide to assist with placement of the stent graft including the first cuff member before deployment of the first cuff member.

In certain embodiments, a rigid support rod 252 is disposed between primary flexible support guide 248 and handle 202. For example, one end of rigid support rod 252 can be connected to distal end 210 of handle 202 and another end can be connected to the proximal end of primary flexible support guide 248. When present, support rod 252 can provide an initial curvature to aid in positioning the stent graft in the natural curvature of the aorta.

Delivery system 200 can also comprise a first actuator 226 comprising a knob 228 and a wire 230 extending from knob 228. Wire 230 can slidably extend through first actuator aperture 218, the first actuator channel and distal first actuator aperture 220. Delivery system 200 can further include a second actuator 238 that also comprises a knob 240 and a wire 242 extending from knob 240. Wire 242 can slidably extend through second actuator aperture 224, the second actuator channel and distal aperture 212. Both wires 230 and 242 can have rounded ends. Distal ends of wires 230 and 242 of respective first and second actuators 226 and 238 can be connected to elongated body 48C of stent graft 34C and first cuff member 74C and can constrain these components within a sheath disposed about each component until stent graft 34C is deployed by retracting knobs 228 and 240 to release respective wires 230 and 242. This effectively "unlaces" the sheaths disposed about the elongated body of the stent graft and the first cuff member of the stent graft to allow expansion of the stent graft as illustrated in FIGS. 3-5. In particular, in a loaded configuration, the elongated body of the stent graft is disposed about the primary flexible support guide proximal to the blunt distal tip and a compression sleeve disposed about the elongated body is connected to a distal portion of the wire of the first actuator. Further, in a loaded configuration, the first cuff member is disposed about a distal portion of the elongate secondary support guide and a compression sleeve disposed about the first cuff member is connected to a distal portion of the wire of the second actuator.

Endovascular Graft Systems

Certain aspects of the present disclosure can include endovascular graft systems comprising a delivery system and an endovascular graft as described above. As illustrated in FIG. 11, in a loaded configuration, the elongated body 48C of stent graft 34C of endovascular graft 10C can be disposed about the primary flexible support guide 248 proximal to tip 250 and can be connected to a distal portion of wire 230 of first actuator 226. First cuff member 74C can be disposed about a distal portion of elongate secondary support guide 254 and can be connected to a distal portion of wire 242 of second actuator 238.

An endovascular graft can be supplied sterile and pre-loaded on a delivery system or loaded onto a delivery system by the user. Delivery system 200 can be a single use 30 French device that includes, as described above, a primary flexible support guide 248 with an atraumatic tip 250 and release wires 230 and 242 to constrain stent graft 34C prior to deployment. A compression sleeve can be located externally on the elongated body 48C and first cuff member 74C of stent graft 34C to constrain the diameter of stent graft 34C when located in the descending aorta and the left subclavian artery respectively. The compression sleeve can be a single unitary sheath or two separate sheaths for each of stent graft 34C and first cuff member 74C. The compression sleeve can remain permanently in the patient's body between the stent graft 34C and the vessel wall.

Methods

Figure 14:
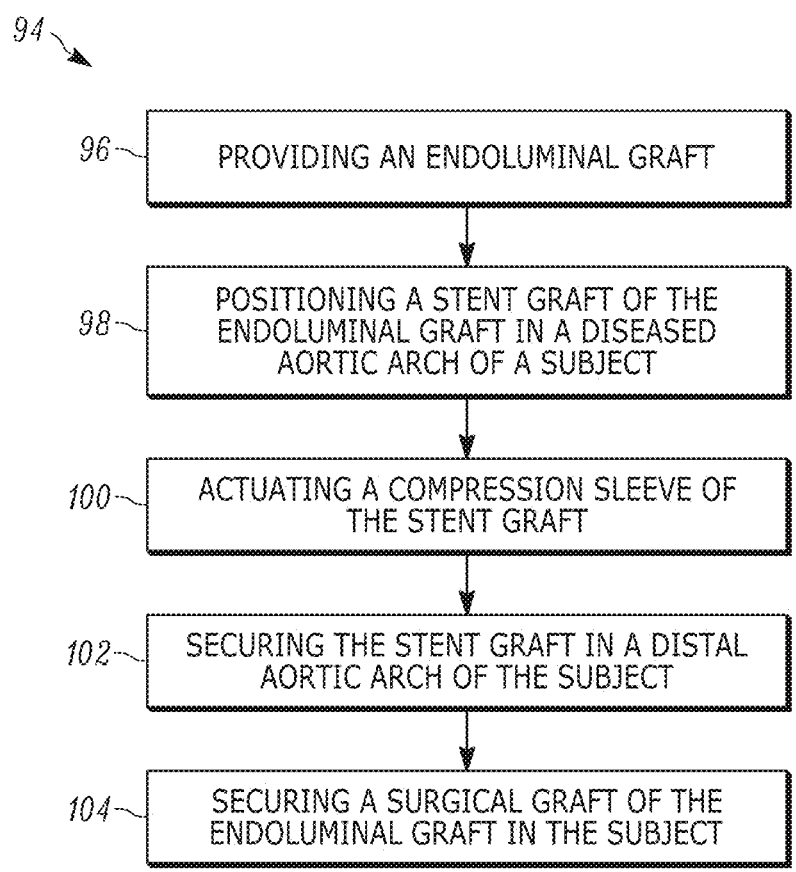
FIG. 14 is a process flow diagram illustrating a method for repairing at least a portion of a diseased aortic arch according to an aspect of the present disclosure.

Another aspect of the present disclosure can include a method 94 (FIG. 14) for repairing a diseased blood vessel in a subject, such as an aneurysm of the aortic arch 12. The method 94 can include the steps of: providing an endoluminal graft (Step 96); positioning a stent graft of the endovascular graft, in a collapsed configuration, in the aortic arch of the subject (Step 98); actuating a compression sleeve of the stent graft so that the stent graft expands into the distal aortic arch and the first cuff member extends into an aortic arch branch vessel (Step 100); securing the stent graft in the distal aortic arch (Step 102); and securing the surgical graft to a transected edge of the aorta (Step 104). In some instances, the method 94 can be used to treat DeBakey type I acute aortic dissections. For example, the method 94 can be adapted based on the procedure of Roselli et al., *J Thorac Cardiovasc Surg.*, 145(3 Suppl):S197-201 (March 2013). The method 94 can also be used for repair of thoracic aorta disease in both ascending arch and descending thoracic aorta (Svensson et al., *Ann Thorac Surg.*, 96:548-58 (2013)).

To repair an aortic arch aneurysm, for example, a surgical procedure using the endovascular graft 10 shown in FIGS. 2A-2B can be employed. The operation can be performed under general anesthesia using cardiopulmonary bypass. The subject can be cooled to at least 28° C., but as low as 18° C. Subject circulation can be arrested or reduced.

Although implantation of the endovascular graft is described below using an open surgical approach, it will be appreciated that other methods for implanting the endovascular graft, such as a percutaneous or minimally invasive surgical technique may be used, as well as other configurations of the endovascular graft described herein.

After providing an endovascular graft at Step 96, a placement position for the endovascular graft in the aortic arch can be determined using an imaging technique, such as, for example, fluoroscopy, angiography, ultrasonography, CT, helical CT, CT angiogram, MRI, and/or MR angiography. Prior to implanting the endovascular graft, a delivery tool can be inserted through the stent graft (via the scallop opening of the endovascular graft. The compression sleeve disposed about the stent graft can then be configured to compress the stent graft into the collapsed configuration so that the stent graft is secured about the delivery tool.

After loading the stent graft onto the delivery tool, the delivery tool can be inserted into the aortic arch via an incision. For example, the aorta can be opened and transected at the brachiocephalic artery. A delivery tool can be positioned in an antegrade manner into the descending aorta. The endovascular graft can then be aligned to a proximal edge of the aortic arch and an access wire tracked into the left subclavian artery.

Once the endovascular graft is appropriately positioned in the aortic arch, a constraint wire for the first cuff member can be removed so that the first cuff member tracks or extends into a portion of the left subclavian artery. This can be achieved, at least in part, by a backstop, described above, which is in an erect configuration and thereby extends into the lumen of the first cuff member, thereby assisting the first cuff member to extend into the left subclavian artery (e.g., in the origin of the left subclavian artery).

Next, the suture or wire that extends through the eyelets of the compression sleeve (which maintains the sleeve and stent graft in the collapsed configuration) can be removed, which causes the stent graft to obtain the expanded configuration and thereby fully expand into the descending aorta. If it has not been done so already, the constraint wire associated with the first cuff member can be removed to allow the first cuff member to fully expand into the left subclavian artery. Any additional components, such as the delivery tool, can also be removed.

Next, gross examination can be performed to verify correct positioning of the great vessel relative to the stent graft. Once the correct position has been verified, the perimeter of the stent graft defining the scallop opening can be secured within the aortic arch (e.g., by suturing). The sewing cuff of the surgical graft can then be sutured to the edge of the transected aorta and the opposing end of the surgical graft sutured to the native unresected ascending aortic root. Thereafter, the vessels surrounding the endovascular graft can be unclamped so that blood can flow normally through the endovascular graft. It will be appreciated that expansion and implantation of the endovascular graft may be varied as needed.

Figure 15:
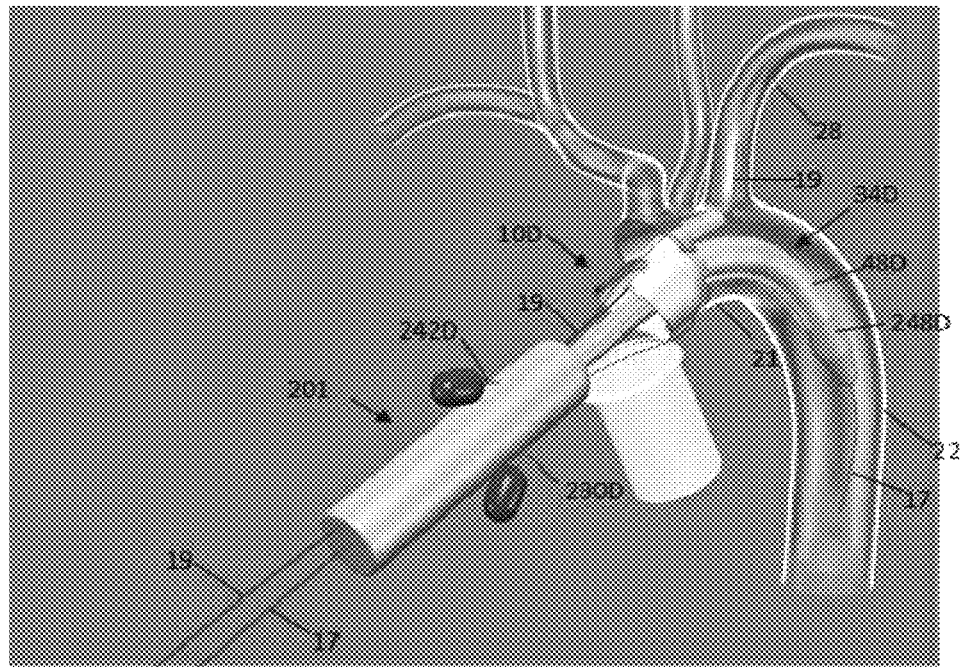
FIGS. 15-19 are schematic illustrations depicting steps of a method of repairing at least a portion of a diseased aortic arch according to an aspect of the present disclosure.

With reference to FIGS. 15-19, another non-limiting example of a method of delivering an endovascular graft will now be described. The endovascular graft can be delivered via access through an open surgical site using the delivery system as described above or another suitable delivery system. The surgical procedure can be performed under general anesthesia using cardiopulmonary bypass with a sternotomy. The patient's temperature can be cooled to at least 28° C., but as low as 18° C. using selective antegrade brain perfusion. Patient circulation can be arrested or reduced. The aorta can be opened and a conventional dissection repair (hemi-arch approach) can be performed; the aorta can be transected just proximal to the brachiocephalic artery to expose the aortic arch 21. As depicted in FIG. 15, a guidewire 17, such as a standard 0.035" guidewire, located within a wire port of a delivery system 201 can be placed into the descending aorta 22. Next, another guidewire 19, such as a 0.035" guidewire, that is pre-loaded through a wire port on delivery system 201 can be placed into the left subclavian artery 28. If delivery system 201 includes a primary flexible support guide as described above (and depicted as primary flexible support guide 248D in FIGS. 15-18), the primary flexible support guide is flexible and can be shaped to accommodate arch morphology. Elongated body 48D of stent graft 34D of endovascular graft 10D can be advanced in an antegrade fashion into the descending aorta 22, with the ability to remove and reshape or bend primary flexible support guide 248D to accommodate the patient's anatomy.

Figure 16:
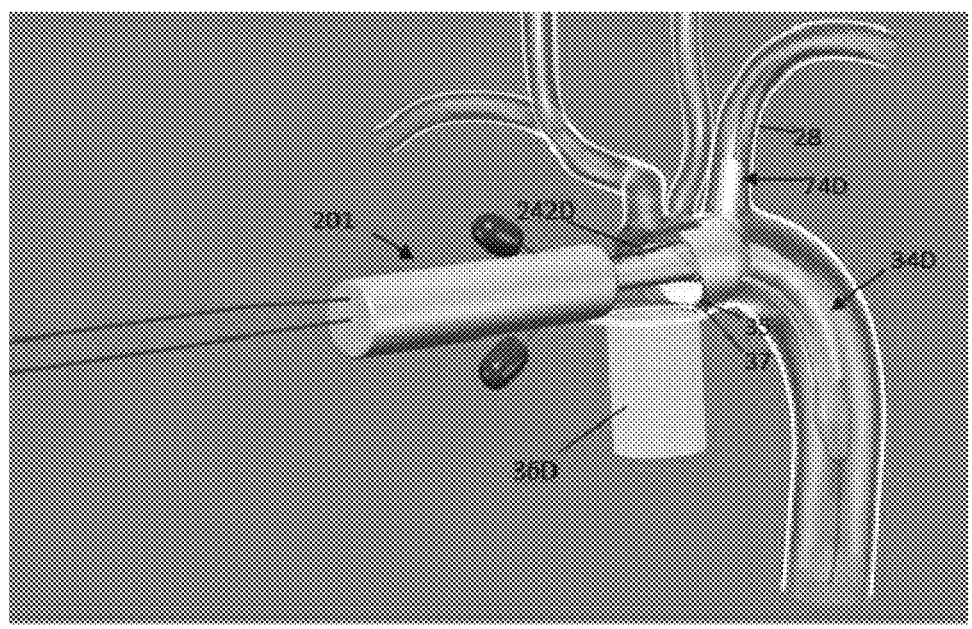
Figure 17:
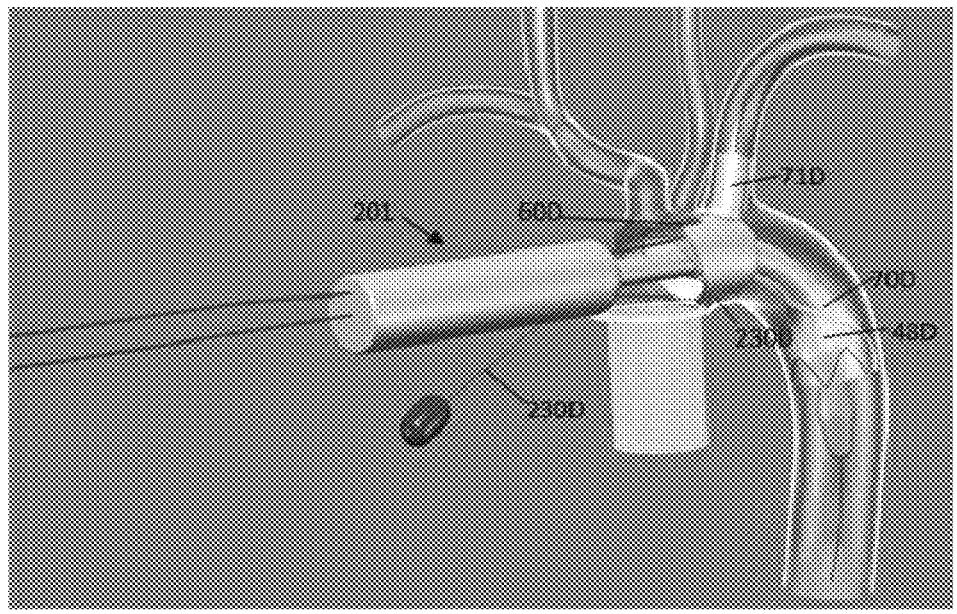
Figure 18:
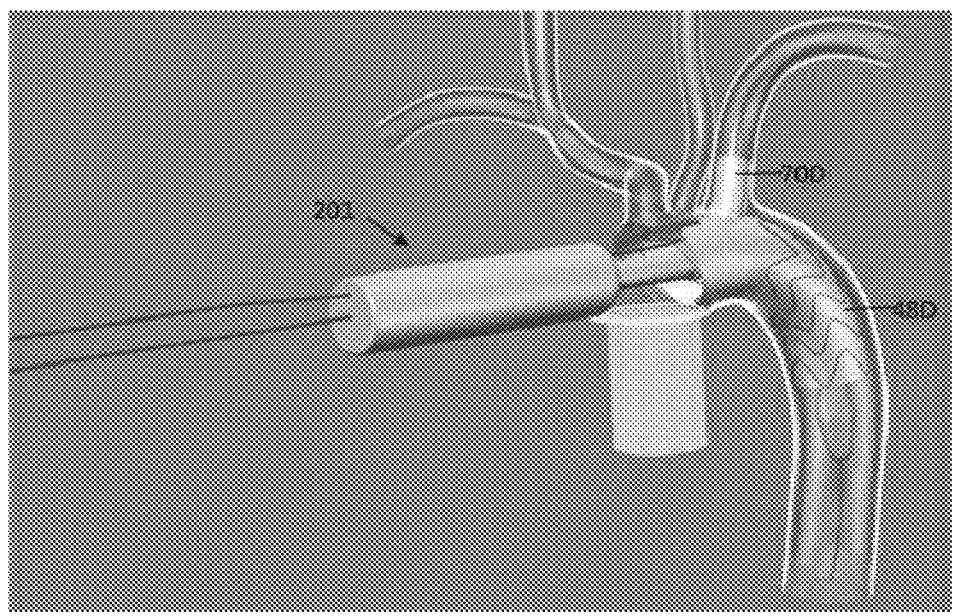

In parallel, first cuff member 74D of stent graft 34D can be inserted and aligned into the left subclavian artery 28, following the guidewire advancement. The user has complete visualization of the device alignment and insertion for positioning of stent graft 34D of endovascular graft 10D. The proximal edge 35 of stent graft 34D is aligned to the proximal edge 37 of the aortic arch 21 as depicted in FIG. 16. If a secondary support guide 254 for the left subclavian artery guidewire is included in the delivery system, such secondary support guide can be retracted and removed, ensuring the guidewire remains in place as depicted in FIGS. 15-17. After correct positioning of the stent graft 34D including first cuff member 74D is confirmed, the user can deploy stent graft 34D. In particular, wires 230 and 242 can be removed in a stepwise fashion. First, wire 242D on the first cuff member 74D can be removed, which "unlaces" a compression sleeve 71D, as described above, and allows first cuff member 74D to fully expand as shown in FIG. 17. Second, wire 230D for compression sleeve surrounding elongated body 48D can be removed, allowing the elongated body 48D of stent graft 34D to expand as shown in FIGS. 17 and 18. The guidewires and delivery system 201 can then be removed. This completes the endovascular delivery and deployment portion of the procedure.

Figure 19:
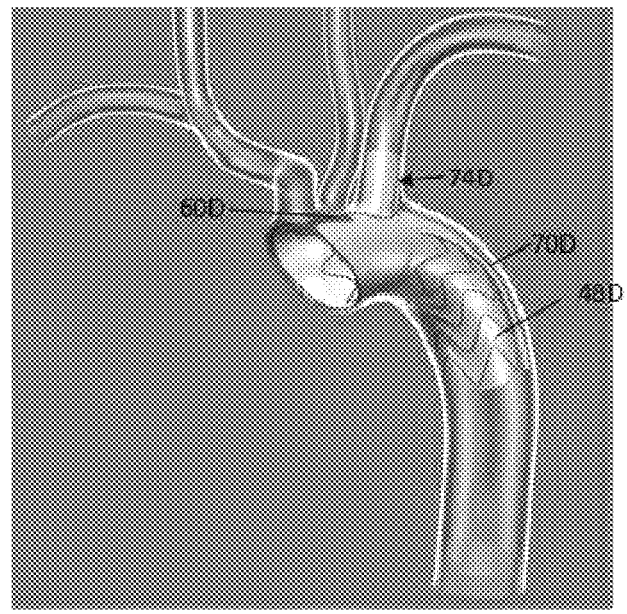

The relative position of stent graft 34D to the great vessels can be examined. The user has the ability to manipulate endovascular graft 10D to position it within the vessels. Additional tissue may be trimmed from the aorta if necessary. The user can assure scallop opening 60D is appropriately aligned around the two remaining branch vessels prior to suturing. The perimeter of stent graft 34D defining scallop opening 60D can be sutured within the aortic arch as depicted in FIG. 19. In particular, sutures can be placed at the base of scallop opening 60D to secure stent graft 34D to the aortic wall and sutures can be placed circumferentially around the proximal edge of stent graft 34D, encompassing scallop opening 60D as illustrated in FIG. 19. In this manner, the entire open edge of the proximal end of stent graft 34D can be sutured to the outer curve of the aortic arch, distal to the left common carotid artery. Once the proximal end of stent graft 34D is securely sewn and sealed in Zone 2 of the native vessel, the sewing cuff of the surgical graft 36D can be sutured to the edge of the transected aorta proximal to the brachiocephalic artery. The combination of these two suture lines forms the opening for the brachiocephalic and carotid vessels. The proximal end of surgical graft 36D can be sutured to the native tissue near the sinotubular junction, supplemented with a strip of graft material.

It will be appreciated that the order of steps described above for implanting an endovascular graft are intended to be illustrative only and are not intended to limit the present disclosure to the order of steps described herein. Further, while some components of an endovascular graft are described as being attached or coupled to other components, such components can be integral with other components. For example, the sewing cuff can be integral with the surgical graft. All patents, patent applications, and publications cited herein are incorporated by reference in their entirety.

The following is claimed:

1. An endovascular graft comprising:
    a stent graft including:
        an elongated body movable between a constrained configuration and an expanded configuration, the elongated body having a proximal end portion, a distal end portion, an intermediate portion extending between the proximal and distal end portions, and a lumen extending between the proximal and distal end portions, the elongated body further including a frame structure having a portion covered by a compression sleeve that retains the body in the constrained configuration until deployment of the stent graft is needed;
        a first cuff member attached to the elongated body and moveable between a constrained configuration and expanded configuration, the first cuff member having a lumen in fluid communication with the lumen of the elongated body, the first cuff member sized and dimensioned to extend into a lumen of an aortic arch branch vessel when the endovascular graft is implanted in a subject, the first cuff member having a compression sleeve disposed thereon that retains the first cuff member in the constrained configuration until deployment of the first cuff member is needed;
        wherein the elongated body includes an aperture in fluid communication with the lumen of the elongated body and the lumen of the first cuff member, the aperture being defined by a portion of the frame structure, the frame structure including a backstop sized and dimensioned to extend into the lumen of the first cuff member when the endovascular graft is implanted in the subject; and
    a surgical graft partially attached to the stent graft at the proximal end portion thereof, wherein a proximal end of the surgical graft includes a sewing cuff attached thereto.

2. The endovascular graft of claim 1, wherein the proximal end portion of the elongated body of the stent graft defines a scallop opening having an arch-shape that is sized and dimensioned to accommodate a delivery tool.

3. The endovascular graft of claim 1, wherein the sewing cuff and the proximal end portion of the elongated body of the stent graft define opposing scallop openings, each scallop opening having an arch-shape that is sized and dimensioned to accommodate a delivery tool.

4. The endovascular graft of claim 1, wherein the intermediate and distal end portions of the elongated body of the stent graft each include an expandable support member having a surface thereof covered by a biocompatible graft material.

5. The endovascular graft of claim 1, wherein the first cuff member is sized and dimensioned for insertion to a left subclavian artery.

6. The endovascular graft of claim 1, wherein the first cuff member comprises a body having a first end portion, a second end portion, and a lumen extending between the first and second end portions, the first and second end portions further including a base ring and an expandable support member, respectively, that are covered with a biocompatible graft material.

7. The endovascular graft of claim 1, wherein the surgical graft includes second and third cuff members that are spaced apart from one another and sized and dimensioned for insertion into the left common carotid artery and the brachiocephalic trunk, respectively.

8. The endovascular graft of claim 1, wherein a portion of the frame structure is disposed at the proximal end portion of the stent graft and comprises a continuous frame comprising the backstop located between arch-shaped frame segments attached to proximal edges of the proximal end portion of the stent graft, the proximal edges partially defining an opening and being in communication with the brachiocephalic artery and the left common carotid artery when the endovascular graft is implanted.

* * * * *